(12) United States Patent
Vandenabeele et al.

(10) Patent No.: US 9,919,048 B2
(45) Date of Patent: Mar. 20, 2018

(54) TARGETING OF INTERLEUKIN-1 AND -18 SIGNALING IN TREATMENT OF SEPTIC SHOCK

(71) Applicants: VIB VZW, Ghent (BE); UNIVERSITEIT GENT, Ghent (BE)

(72) Inventors: Peter Vandenabeele, Sint-Amandsberg (BE); Anje Cauwels, Merelbeke (BE); Tom Vandenberghe, Haasdonk (BE)

(73) Assignees: VIB VZW, Ghent (BE); UNIVERSITEIT GENT, Ghent (BE)

( * ) Notice: Subject to any disclaimer, the term of this patent is extended or adjusted under 35 U.S.C. 154(b) by 0 days.

(21) Appl. No.: 15/111,374

(22) PCT Filed: Jan. 15, 2015

(86) PCT No.: PCT/EP2015/050679
§ 371 (c)(1),
(2) Date: Jul. 13, 2016

(87) PCT Pub. No.: WO2015/110346
PCT Pub. Date: Jul. 30, 2015

(65) Prior Publication Data
US 2016/0331837 A1 Nov. 17, 2016

(30) Foreign Application Priority Data
Jan. 21, 2014 (GB) .................................. 1400997.1

(51) Int. Cl.
*A61K 39/395* (2006.01)
*A61K 39/00* (2006.01)
*A61K 38/17* (2006.01)
*C07K 16/24* (2006.01)
*A61K 38/20* (2006.01)
*C07K 16/28* (2006.01)

(52) U.S. Cl.
CPC .......... *A61K 39/3955* (2013.01); *A61K 38/17* (2013.01); *A61K 38/1793* (2013.01); *A61K 38/20* (2013.01); *C07K 16/244* (2013.01); *C07K 16/2866* (2013.01); *A61K 2039/505* (2013.01); *A61K 2039/507* (2013.01); *C07K 2317/76* (2013.01)

(58) Field of Classification Search
None
See application file for complete search history.

(56) References Cited

U.S. PATENT DOCUMENTS 8,431,130 B2 * 4/2013 Ghayur .................. C07H 21/04
424/130.1
8,518,407 B2 * 8/2013 Varnum ............. C07K 16/2866
424/144.1
2013/0156760 A1 6/2013 Fraunhofer et al.

FOREIGN PATENT DOCUMENTS

| AU | 2012216429 A1 | 9/2012 |
|---|---|---|
| WO | 2003/045400 A1 | 6/2003 |
| WO | 2005/063290 A2 | 7/2005 |
| WO | 2010/066740 A1 | 6/2010 |

OTHER PUBLICATIONS

Arend et al. (2008) "IL-1, IL-18, and IL-33 families of cytokine," Immunol Rev 223:20-38.
Dimitrov (2009) "Engineered CH2 domains (nanoantibodies)," mAbs 1:26-28.
Dinarello et al. (2011) "Interleukin-1 in the pathogenesis and treatment of inflammatory diseases," Blood. 117 (14):3720-3732.
Duprez et al. (2011) "RIP kinase-dependent necrosis drives lethal systemic inflammatory response syndrome," Immunity 35:908-918.
Fantuzzi et al. (1996) "Effect of endotoxin in IL-1 beta-deficient mice," J Immunol 157:291-296.
Fantuzzi et al. (1996) "The inflammatory response in interleukin-1 beta-deficient mice: Comparison with other cytokine-related knock-out mice," J Leukoc Biol 59:489-491.
Ferrari et al. (2006) "The p2x7 receptor a key player in IL-1 processing and release," J Immunol 176:3877-3883.
Fischer et al. (1992) "Interleukin-1 receptor blockade improves survival and hemodynamic performance in *Escherichia coli* septic shock, but fails to alter host responses to sublethal endotoxemia," J Clin Invest 89:1551-1557.
Franchi et al. (2009) "The inflammasome: A caspase-1-activation platform that regulates immune responses and disease pathogenesis," Nat Immunol 10:241-247.
Franchi et al. (2010) "Inflammasomes as microbial sensors," Eur J Immunol 40:611-615.
Ghayur et al. (1997) "Caspase-1 processes IFN-γ-inducing factor and regulates LPS-induced IFN-γ production," Nature 386:619-623.
Glaccum et al. (1997) "Phenotypic and functional characterization of mice that lack the type I receptor for IL-1," J Immunol 159:3364-3371.
Godshall et al. (2002) "Genetic background determines susceptibility during murine septic peritonitis," The Journal of Surgical Research 102:45-49.
Gu et al. (1997) Activation of Interferon-γ Inducing Factor Mediated by Interleukin-1β Converting Enzyme, Science 275:206-209.
Hayashi et al. (2002) "Efficient gene modulationin mouse epiblast using a sox2cre transgenic mouse strain," Mech. Dev. 119(Suppl 1):S97-S101.
Hochholzer et al. (2000) "Role of interleukin-18 (IL-18) during lethal shock: Decreased lipopolysaccharide sensitivity but normal superantigen reaction in IL-18-deficient mice," Infect Immun 68:3502-3508.

(Continued)

*Primary Examiner* — Shulamith H Shafer
(74) *Attorney, Agent, or Firm* — Lathrop Gage LLP; James H. Velema, Esq.

(57) ABSTRACT

The present invention relates to the inactivation of interleukin-1 and interleukin-18 signaling in treatment of inflammation and septic shock. More specifically, it relates to a sequential or simultaneous application of both an interleukin-1 receptor antagonist and an interleukin-18 antibody. In one preferred embodiment, a combination treatment of an IL-1 receptor antagonist and an IL-18 antibody is used.

17 Claims, 9 Drawing Sheets

(56) References Cited

OTHER PUBLICATIONS

Horneff (Jan. 5, 2013) "Update on biologicals for treatment of juvenile idiopathic arthritis," Expert Opin Biol Ther 13:361-376.
Hoshino et al. (1999) "Cutting edge: Toll-like receptor 4 (TLR4)-deficient mice are hyporesponsive to lipopolysaccharide: Evidence for TLR4 as the Lps gene product," J Immunol 162:3749-3752.
Hotchkiss et al. (2010) "Immunotherapy for sepsis—a new approach against an ancient foe," N Engl J Med 363:87-89.
Joosten et al. (2010) "Differential susceptibility to lethal endotoxaemia in mice deficient in IL-1 alpha, IL-1 beta or IL-1 receptor type I," APMIS 118:1000-1007.
Kanneganti et al. (2007) "Pannexin-1-mediated recognition of bacterial molecules activates the cryopyrin inflammasome independent of toll-like receptor signaling," Immunity 26:433-443.
Kawai et al. (1999) "Unresponsiveness of myd88-deficient mice to endotoxin," Immunity 11:115-122.
Kayagaki et al. (2011) "Non-canonical inflammasome activation targets caspase-11," Nature 479:117-121.
Kolmar (2008) "Alternative binding proteins: biological activity and therapeutic potential of cysteine-knot miniprotems," FEBS J. 275:2684-2690.
Kuida et al. (1995) "Altered cytokine export and apoptosis in mice deficient in interleukin-1 beta converting enzyme," Science 267:2000-2003.
Lamkanfi et al. (2009) "Caspase-7 deficiency protects from endotoxin-induced lymphocyte apoptosis and improves survival," Blood 113:2742-2745.
Lamkanfi et al. (2010) "Inflammasome-dependent release of the alarmin hmgbl in endotoxemia," J Immunol 185:4385-4392.
Li et al.(1995) "Mice deficient in IL-1 beta-converting enzyme are defective in production of mature IL-1 beta and resistant to endotoxic shock," Cell 80, 401-411.
Lochner et al. (2002) "Generation of neutralizing mouse anti-mouse IL-18 antibodies for inhibition of inflammatory responses in vivo," J Immunol Methods 259:149-157.
Mariathasan et al. (2006) "Cryopyrin activates the inflammasome in response to toxins and atp," Nature 440:228-232.
Miao et al. (2011) "Caspase-1-induced pyroptotic cell death," Immunol Rev 243:206-214.
Netea et al. (2000) "Neutralization of IL-18 reduces neutrophil tissue accumulation and protects mice against lethal *Escherichia coli* and *Salmonella typhimurium* endotoxemia," J Immunol 164:2644-2649.
Nygren (2008) "Alternative binding proteins: aftibody binding proteins developed from a small three-helix bundle scaffold," FEBS J. 275:2668-2676.
Ohlsson et al. (1990) "Interleukin-1 receptor antagonist reduces mortality from endotoxin shock," Nature 348:550-552.
Pelegrin et al. (2006) "Pannexin-1 mediates large pore formation and interleukin-1 beta release by the atp-gated p2x7 receptor," EMBO J 25:5071-5082.
Pelegrin et al. (2009) "The P2X(7) receptor-pannexin connection to dye uptake and IL-1beta release," Purinergic Signal 5:129-137.
Poltorak et al. (1998) "Defective LPS Signaling in C3H/HeJ and C57BUL/10ScCr Mice: Mutations in Tlr4 Gene," Science 282:2085-2088.
Qureshi et al. (1999) "Endotoxin-tolerant mice have mutations in toll-like receptor 4 (TLR4)," J Exp Med 189:615-625.
Rittirsch et al. (2009) "Immunodesign of experimental sepsis by cecal ligation and puncture," Nat Protoc 4:31-36.
Skerra (2008) "Alternative binding proteins: anticalins—harnessing the structural plasticity of the lipocalin ligand pocket to engineer novel binding activities," FEBS J. 275:2677-2683.
Stumpp et al. (2007) "DARpins: a true alternative to antibodies," Curr. Opin. Drug Discov. Devel. 10:153-159.
Taveira Da Silva et al. (1993) "Brief report: Shock and multiple-organ dysfunction after self-administration of *Salmonella* endotoxin," N Engl J Med 328:1457-1460.
Tramontano et al. (1994) "The making of the minibody: An engineered β-protein for the display of conformationally constrained peptides," J. Mol. Recognition 7:9-24.
Wang et al. (2005) "Endotoxemic acute renal failure is attenuated in caspase-1-deficient mice," Am. J. Physiol. Renal Physiol. 288:F997-1004.
Wesolowski et al. (2009) "Single domain antibodies: promising experimental and therapeutic tools in infection and immunity," Med. Microbiol. Immunol. 198:157-174.
International Search Report with Written Opinion corresponding to International Patent Application No. PCT/EP2015/050679, dated Apr. 2, 2015.

* cited by examiner

TARGETING OF INTERLEUKIN-1 AND -18 SIGNALING IN TREATMENT OF SEPTIC SHOCK

RELATED APPLICATIONS

This application is a 35 U.S.C. § 371 filing of International Application No. PCT/EP2015/050679, filed Jan. 15, 2015, which claims priority to Great Britain Patent Application No. 1400997.1, filed Jan. 21, 2014, each of which is incorporated herein by reference in its entirety.

The present invention relates to the inactivation of interleukin-1 (IL-1) and interleukin-18 (IL-18) signaling in treatment of inflammation and septic shock. More specifically, it relates to a sequential or simultaneous application of both an IL-1 receptor (IL-1R) antagonist and an interleukin-18 antibody. In one preferred embodiment, a combination treatment of an IL-1R antagonist and an IL-18 antibody is used.

Sepsis remains the leading cause of death in intensive care units (ICUs), despite remarkable advances in the treatment of critical illnesses and outstanding progress in all other aspects of ICU medicine (Hotchkiss and Opal, 2010). Although the prevailing concept has long been that mortality in sepsis results from an unbridled hyper-inflammatory cytokine-mediated response, the failure of dozens of clinical trials to treat sepsis by controlling several of these cytokine responses demonstrates that the molecular mechanisms behind the progression of sepsis are still poorly understood (Hotchkiss and Opal, 2010). In humans, intravenous injection of larger doses of endotoxin leads to hypotensive shock and multiple organ dysfunction (Taveira da Silva et al., 1993). Considering its sepsis-like effects, including fever, hypothermia, tachypnea, tachycardia, cardiovascular collapse and organ dysfunction, LPS injection has been widely used as an experimental model for sepsis.

Typically, LPS activates Toll-like receptor 4 (TLR4) (Poltorak et al., 1998). In addition, the intracellular NOD-like receptor family member NLRP3 (also known as cryopyrin, CIAS or NALP3) is activated directly or indirectly (Kanneganti et al., 2007). Mice deficient in one of these receptors are protected against LPSinduced lethal shock (Hoshino et al., 1999; Qureshi et al., 1999; Mariathasan et al., 2006), and both receptors are required to induce the production of the inflammatory cytokines interleukin-1β (IL-1β) and IL-18 (Franchi et al., 2009). The proteolytic activity of caspase-1 (CASP1) is important for the maturation of proIL-1β (Li et al., 1995; Kuida et al., 1995) and proIL-18 (Ghayur et al., 1997; Gu et al., 1997), and for the induction of pyroptosis (Miao et al., 2011). The current view is that TLR4 mediates the transcriptional upregulation of both inactive pro-forms, while NLRP3 inflammasome triggering mediates the activation of CASP1 and the subsequent proteolytic activation and release of mature IL-18 and IL-18 (Franchi et al., 2010). To date, two non-exclusive models for CASP1 activation have been hypothesized. First, $K^+$ efflux was identified as an important costimulatory event in LPS-mediated CASP1 activation (Pelegrin and Suprenant, 2009). Later, a model in which the pannexin-1 pore is activated by ATP through P2X7R was put forward as a conduit for the delivery of microbial molecules such as LPS to the host cytosol, which could then trigger NLRP3 activation (Kanneganti et al., 2007; Ferrari et al., 2006; Pelegrin and Suprenant, 2006).

The central role of CASP1, the prototype inflammatory caspase, in the pathology of endotoxemia has been extensively reported (Li et al., 1995; Netea et al., 2000; Lamkamfi et al., 2009). However, the contribution of CASP1 and its possible substrates IL-1β, IL-18 and caspase-7 (CASP7) remains confusing. Recently, Casp1 targeted mice were found to carry a 129 ES cell-derived inactivating mutation in their caspase-11 (Casp11) gene locus, which seemed partially responsible for their resistance to endotoxic shock (Kayagaki et al., 2011). Downstream of CASP1, contradicting results have been reported regarding the contribution of its substrates. Transgenic mice overexpressing IL-1R antagonist (Ohlsson et al., 1990; Fischer et al., 1992) or lacking the genes for IL-1R type I (IL-1R1) (Joosten et al., 2010), IL-1β (Netea et al., 2000), IL-18 (Hochholzer et al., 2000) or CASP7 (Lamkanfi et al., 2009) have been reported to be less sensitive to LPS. In sharp contrast, several other studies excluded a role for IL-1 or IL-18, as they found that mice deficient in IL-1β (Joosten et al., 2010, Fantuzzi et al., 1996), IL-1R1 (Glaccum et al, 1997; Kawai et al., 1999), IL-18 (Kawai et al., 1999) or IL-1β/18 (Lamkanfi et al., 2010) were not protected. In agreement with those results, Wang et al. (2005) could not show any protection using an IL-1R antagonist in combination with an IL-18 neutralizing antiserum. The IL-1 family contains two agonists, IL-1α and IL-1β, a specific inhibitor, IL-1R antagonist, and two receptors, the biologically active IL-1R type I, IL-1R1, and the inhibitory type II, IL-1R2 (Arend et al., 2008).

Surprisingly, we found, in a comprehensive study in mice deficient in IL-1β, IL-18 or CASP7 (or combinations of these), that mice wherein both IL-1 activity and IL-18 activity are inhibited are protected in three different inflammatory/septic shock models (LPS-induced shock model, TNF-induced SIRS and CLP), and confirmed the therapeutic potential of the inhibition of the central players IL-1R1 and IL-18 using a combination of an IL-1R antagonist and an IL-18 antibody.

A first aspect of the invention is a combination of an IL-1R antagonist and an IL-18 antibody for use in treatment of sepsis. In one preferred embodiment, the IL-1R antagonist and the IL-18 antibody are given simultaneously. Simultaneously as used here includes both the administration in one pharmaceutical composition, as well as the simultaneous administration of the pharmaceutical compositions wherein one comprises the IL-1R antagonist and the other the IL-18 antibody. In another preferred embodiment the IL-1R antagonist and the IL-18 antibody are given sequentially. Sequentially, as used here, means that either the IL-1R antagonist or the IL-18 antibody is administered first, followed by the administration of the IL-18 antibody or the IL-1R antagonist, respectively. Preferable, the maximum time period between the two administrations is 5 hours, even more preferably, it is 4 hours, more preferably 3 hours, more preferably 2 hours, more preferably one hour, most preferably the IL-1R antagonist and the IL-18 antibody are administered directly one after the other. IL-1R, as used herein, refers to the IL-1R type I (IL-1R1), primarily responsible for transmitting the inflammatory effects of IL-1. An IL-1R antagonist, as used here, may be any molecule capable of binding to the IL-1R in a specific way and inhibiting (neutralizing) IL-1 induced signaling. Preferably, said IL1-R antagonist is selected from the group consisting of the recombinant, non-glycosylated version of the human IL-1R antagonist, designated as Anakinra and a neutralizing IL-1R antibody. Antibodies as used here include, but are not limited to heavy chain antibodies (hcAb), single domain antibodies (sdAb; Wesolowski et al., 2009), minibodies (Tramontano et al., 1994), the variable domain of camelid heavy chain antibodies (VHH), the variable domain of the new antigen receptors (VNAR), affibodies (Nygren et al., 2008), alphabodies (WO2010066740), designed ankyrin-repeat domains (DARPins) (Stumpp and Amstutz., 2007), anticalins (Skerra et al., 2008), knottins (Kolmar et al., 2008) and engineered CH2 domains (nanoantibodies; Dimitrov, 2009). An IL-18 antibody may be any antibody capable of binding to IL-18 in a specific way and inhibiting (neutralizing) the IL-18 induced signaling. In a preferred embodiment, an IL-1R antagonist is used in combination with an IL-18 antibody. In a particular embodiment, the IL-1R antagonist and the IL-18 antibody are one chemically conjugated bispecific molecule. Preferably, said chemically conjugated molecule is a bispecific molecule consisting of two antibodies. Even more preferably, said bispecific molecule consists of two VHH domains.

Treatment, as used here, can be either therapeutic or prophylactic treatment. Preferably, said treatment is a therapeutic treatment.

Another aspect of the invention is a pharmaceutical composition, comprising both an IL-1R antagonist and an IL-18 antibody, according to the invention, preferably with a suitable excipient. In a preferred embodiment, the pharmaceutical composition is a composition for injection.

EXAMPLES

Materials and Methods to the Examples

Mice

Figure 1:
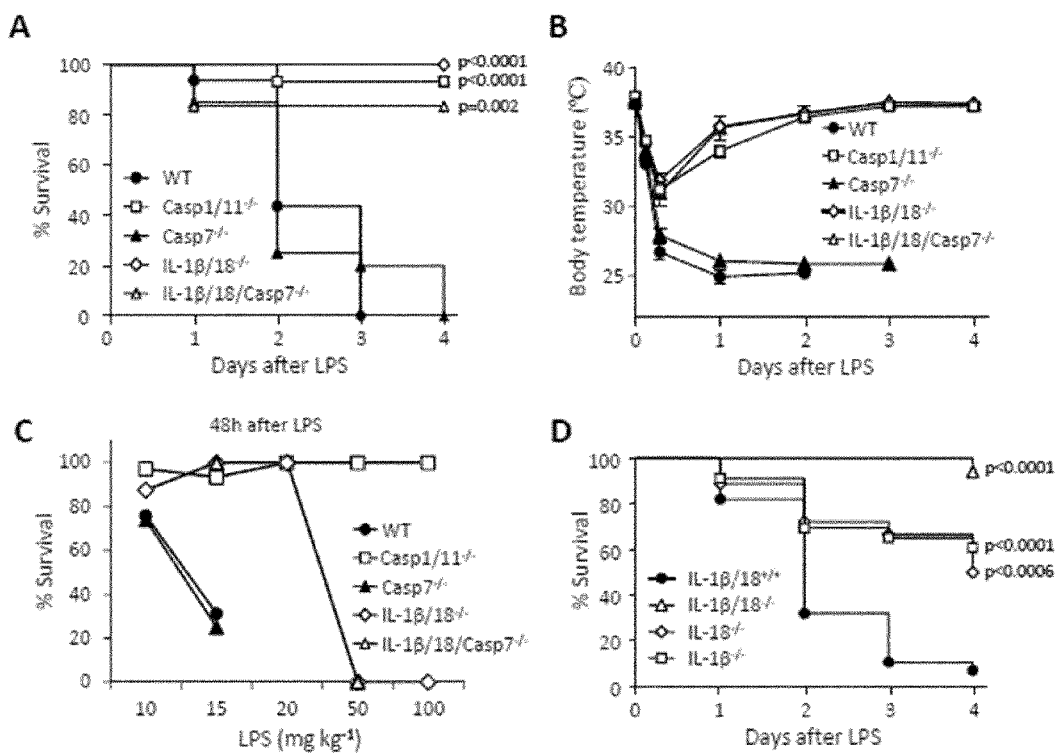
FIG. 1. IL-1β and IL-18 deficiency synergistically protect against a lethal dose of LPS, CASP7-deficiency does not contribute to the protection. Survival (A) and decrease in rectal body temperature (B) were analyzed in function of time in wild-type (WT) [n=16], Casp1/11$^{-/-}$ [n=15], Casp7$^{-/-}$[n=20], IL-1β/18$^{-/-}$[n=17] and IL-1β/18/Casp7$^{-/-}$ [n=6] mice after i.p. injection of 15 mg kg$^{-1}$ LPS (LD$_{100}$). The combined results of three independent experiments are shown. Body temperature data are means±SEM. Statistical difference in hypothermia between Casp1/11$^{-/-}$, IL-1β/18$^{-/-}$ or IL-1β/18/Casp7$^{-/-}$ vs WT is p<0.001. (C) Survival rate (after 48 h) is plotted for WT, Casp1/11$^{-/-}$, Casp7$^{-/-}$, IL-1β/18$^{-/-}$ and IL-1β/18/Casp7$^{-/-}$ mice after i.p. injection with different doses of LPS, ranging from 10 to 100 mg kg$^{-1}$. (D) Survival rate for IL-1β/18$^{+/+}$ (n=29), IL-1β/18$^{-/-}$ (n=17), IL-1β$^{-/-}$ (n=23) and IL-18$^{-/-}$ (n=18) after i.p. injection with 15 mg kg$^{-1}$ LPS.

All mice were bred under specific-pathogen-free (SPF) conditions, and in all experiments sex- and age-matched animals were used. For some crucial experiments littermates where used, as indicated. Mice were housed in temperature-controlled, air-conditioned facilities with 14/10-h light/dark cycles and food and water ad libitum, and were used at the age of 8-12 weeks. All experiments were approved by the animal ethics committee of Ghent University. Conditional Casp7$^{fl/fl}$ were generated on a mixed 129S6/Swiss background and backcrossed for at least 10 generations to the C57BL/6J background before crossing with Sox2Cre mice to generate Casp7$^{-/-}$ mice (Hayashi et al., 2002). Casp1$^{-/-}$ and IL-1β/18$^{-/-}$ mice on a C57BL/6J background were kindly provided by Dr. R. Flavell (Howard Hughes Medical Institute, Chevy Chase, USA), and Dr. A. Zychlinsky (Max Planck Institute, Berlin, Germany), respectively. IL-1β/18/Casp7$^{-/-}$ mice were generated by crossing Casp7$^{-/-}$ with IL-1β/18$^{-/-}$ mice. IL-1β$^{-/-}$ and IL-18$^{-/-}$ mice were generated by intercrossing IL-1β/18$^{+/-}$ mice.

Antagonists

Anakinra (Kineret®) was purchased from Sobi (Stockholm, Sweden). Neutralizing IL-18 antibodies were purified from the supernatant of an anti-IL-18 producing hybridoma cell line generated in the lab of Prof. I. Frster (Lochner et al., 2002) and purified in house. Briefly, the CHO SK11AE4 monoclonal antibody producing cell line was grown in RPMI medium without fetal calf serum in roller flasks. After 96 h, the cell culture supernatant was collected by centrifugation at 1500 rpm for 10 min and EDTA-free Protease Inhibitor Cocktail Tablets (Roche Diagnostics, Brussels, Belgium) were added. The supernatant was filtered using a 0.22 μm bottle top filter (Millipore, Billerica, Mass., USA) and applied to a HiTrap MabSelect Sure column (GE Healthcare, Freiburg, Germany) pre-equilibrated with binding buffer (PBS, pH 7.4). The IL18 mAb was eluted with 100 mM glycine pH 3.0, 50 mM NaCl and immediately neutralized with 1 M Tris-HCl pH 8.0. Fractions containing the mAb were pooled, dialyzed against PBS pH 7.4 using a slide-a-lyzer dialysis cassette (Thermo Scientific, Waltham, Mass., USA), and stored at −70° C. The purity of the protein was >85%. Mice were injected i.p. with vehicle (Veh), Anakinra (745 mg kg-1), anti-IL-18 (20 mg kg-1) or a combination, 1 h and 24 h after i.p. injection of LPS (15 mg kg-1).

Cecal Ligation and Puncture (CLP) Procedure

The CLP procedure is performed according to the general guidelines (Rittirsch et al., 2009). Two different procedures were used (mild or severe) resulting in 50% or 100% lethality in C57BL/6J mice. Briefly, the mice were anesthetized using 2% isoflurane in oxygen. After disinfection of the abdomen, a 10-mm midline laparotomy was performed and the cecum exposed. Using 5-0 Ethicon Mersilk suture, 50% of the cecum was ligated and subsequently perforated by a single through-and-through puncture with a 22G needle (for mild CLP), or 100% of the cecum was ligated and subsequently perforated twice by a through-and-through puncture with a 20G needle (for severe CLP). The abdomen was closed in two layers, using 5-0 suture for the peritoneum and abdominal musculature, and wound clips for the skin. Following surgery, the animals were resuscitated with 1 ml prewarmed 0.9% saline administered subcutaneously (s.c.). In addition, the mice subjected to the severe CLP procedure were treated i.p. with broad-spectrum antibiotics (ciprofloxacin 4 mg kg$^{-1}$, ampicillin 20 mg kg$^{-1}$, metronidazole 20 mg kg$^{-1}$ and vancomycin 10 mg kg$^{-1}$ together in 400 μl PBS) or vehicle (400 μl PBS) daily until day 10. On day 1, the mice received the treatment 5 h after the CLP procedure. Sham operated mice underwent the same procedure but without cecal ligation and puncture. All animals are given pre- and postoperative analgesia (Ibuprofen, 200 μg ml$^{-1}$ in drinking water), starting 24 h before until 48 h after surgery.

Reagents and Injections

Mice were injected intraperitoneally (i.p.) with various doses of E. coli O111:B4 LPS (Sigma-Aldrich, St Louis, Mo., USA) suspended in LPS-free PBS. Mice were injected intravenously (i.v.) with 450 μg kg-1 TNF (purified in house) suspended in LPS-free PBS.

Depletion of Commensal Intestinal Bacteria

For antibiotic-mediated depletion of commensal bacteria, mice were treated with 200 mg L$^{-1}$ ciprofloxacin (Sigma-Aldrich), 1 g L$^{-1}$ ampicillin (Sigma-Aldrich), 1 g L$^{-1}$ metronidazole (Sigma-Aldrich), and 500 mg L$^{-1}$ vancomycin (Labconsult) in their drinking water. After 2 wk, the presence of colonic microflora was determined by culturing fecal samples in both brain heart infusion (BD) and thioglycollate medium (Sigma-Aldrich).

Body Temperature Measurements

Rectal body temperature was recorded with an electronic thermometer (model 2001; Comark Electronics).

LDH, ALT, AST, Creatine Kinase, Creatinine, Troponin T and Plasma Cytokine Determination Blood was collected in tubes containing EDTA (Microvettes, Sarstedt, Numbrecht, Germany) by cardiac puncture using heparin-coated syringes. Plasma was obtained after centrifugation of blood. LDH, ALT, AST, creatine kinase and Troponin T were determined using Cobas 8000 modular analyzer series (Roche Diagnostics, Basel, Switzerland). Plasma cytokine levels were determined using bead-assay-based techniques. IL-1α-, IL-18-, IFNγ-, TNF- and IL-6-levels were determined using Bioplex (Biorad, Calif., USA) and Milliplex kits (Millipore, Mass., USA), while IL-1β-levels were determined using CBA flex sets (BD, Calif., USA).

Histopathology

Histopathology was evaluated on paraffin sections. CD45 staining was performed on deparaffinized slides as follows: Rehydration by standard procedures, 10 min incubation in antigen retrieval buffer (citrate buffer pH6.0) at 95° C., cooling to room temperature, rinsing with distilled water (bidi) and PBS, circling tissue section with DAKO pen, 20 min incubation in peroxidase blocking buffer (0.1% H2O2+ 0.6% NaN3 in PBS), rinsing with bidi and PBS, 20 min in blocking buffer (1:10 goat serum in PBS), incubation with CD45 at 4° C. overnight, rinsing with bidi and PBS, 30 min incubation with rabbit-anti-rat-biotin at RT (1/300 in blocking buffer), 20 min streptavidin/biotin-complex solution (ABC kit, Enzo Life Sciences, Lausen, Switzerland), rinsing with bidi and PBS, 5 min in DAB, rinsing with bidi, 20 sec hematoxylin solution, rinsing in bidi, dehydration by standard procedures, and mounting in depex.

Scoring or Quantification of IHC Stainings

Semi-automatic quantification was performed using Fiji software. To quantify liver immune cell infiltration, 12 bright field images (100×) of CD45+ staining of liver sections (derived from 4 mice/group) were split in separate RGB channels, and the CD45+ area relative to total tissue was measured after manual adaptation of threshold in blue and green channels, respectively.

Statistics

All statistics were performed using Prism software (GraphPad Software, Inc.) or Genstat (Payne et al. Genstat Release 13.1 Reference Manual, Part 3. VSN International, Oxford). Survival curves were compared with a Mantel-Cox test. IHC, serum and plasma parameters are shown as means±SE; they were compared with a one-way analysis of variance test with either a Bonferroni posttest for comparison of all pairs, or a Dunnett posttest for comparison of all data with the control (PBS). Statistical difference in IL-18 levels (FIG. 4C) was calculated using a multiple comparison two-way Anova test. Statistically significant differences in body temperature were calculated using REML implemented in Genstat. To indicate statistical significance, we either indicated the p value, or used * for p<0.05,  for p<0.01, * for p<0.001, **** for p<0.0001.

Statistical Analysis of Body Temperature

Rectal body temperature was monitored in 2-4 sequential experiments. All experiments were set up as a completely randomized design. We used REML as implemented in Genstat (Payne et al. Genstat Release 13.1 Reference Manual, Part 3. VSN International, Oxford) to perform the repeated measurements analysis. Repeated measurements data were analyzed by fitting the following linear mixed model (random terms underlined): yijkl=μ+treatmenti+timek+treatmentxtimeik+experimentj+eijkl, where yijkl is the phenotypic value of the lth individual of genotype i, measured in the ith experiment at time point k; the fixed term "treatment" represents either an effective treatment or a genotype factor, depending on the experiment; random terms in the model were assumed to be independent and ~N(0, 2 t σ), where t=r (experiment) and e (error). Various ways of modeling the correlation structure (uniform, autoregressive order 1 (AR1) or 2 (AR2), and antedependence order 1 and 2) were compared in the residual maximum likelihood (REML) framework. Selection of the best model fit was based on a likelihood ratio test (LRT) statistic and/or the Aikake Information coefficient (AIC). When residuals from the analysis indicated increasing variance over time, this was modeled directly by specifying that heterogeneity is to be introduced into the model. Significance of the fixed main and interaction effects as well as the linear contrasts was assessed by an F test. Fitting linear contrasts amongst the levels of the fixed factor treatment and treatmentxtime in the REML analysis of repeated measurements was done using the FCONTRASTS procedure in Genstat.

Figure 6:
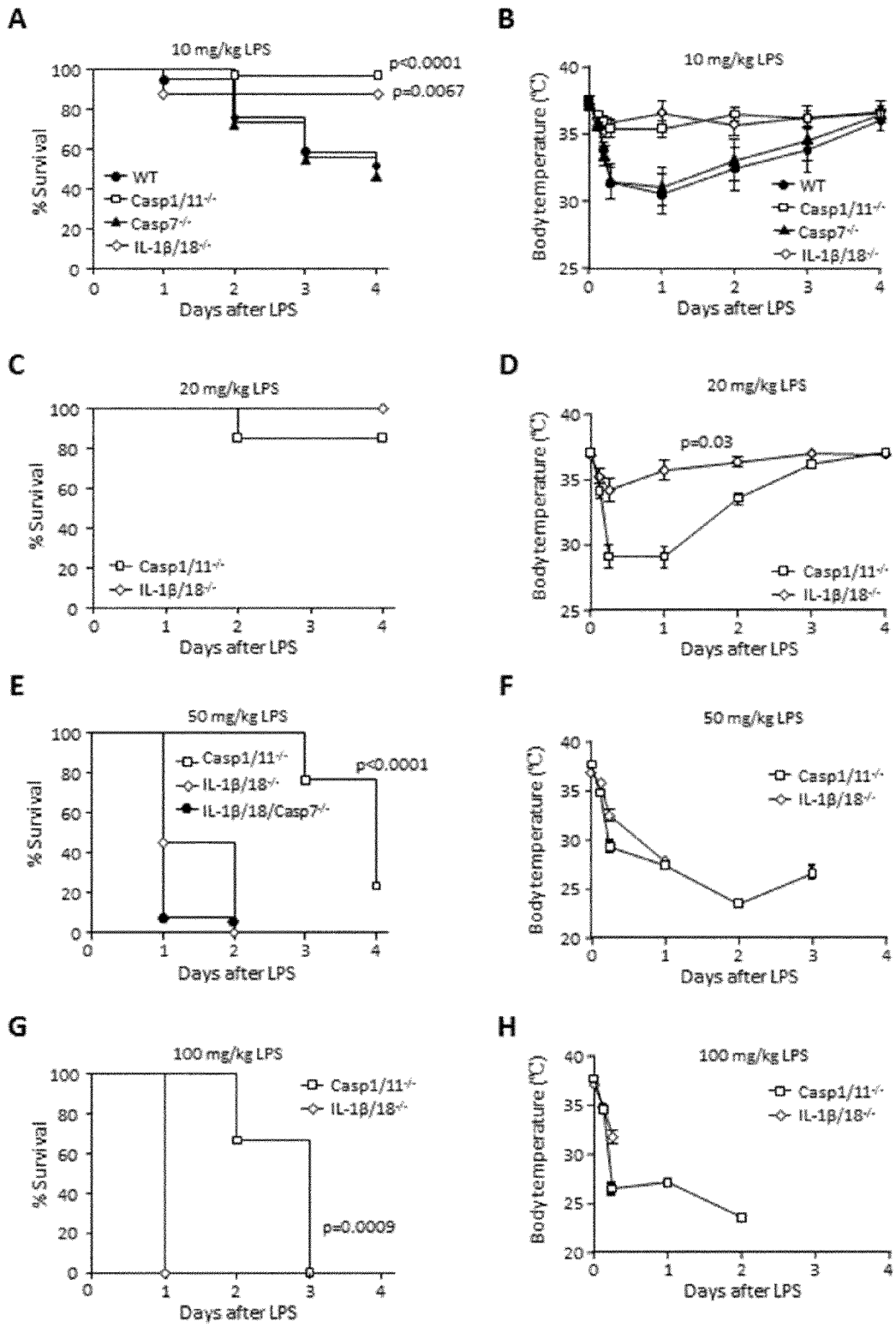
FIG. 6. Survival (A) and decrease in rectal body temperature (B) were analyzed in function of time in WT [n=58], Casp1/11$^{-/-}$[n=35], Casp7$^{-/-}$[n=50] and IL-1β/18$^{-/-}$[n=24] mice after i.p. injection with 10 mg kg$^{-1}$ LPS (LD$_{50}$). The combined results of five independent experiments are shown. Survival (C) and decrease in rectal body temperature (D) were analyzed in function of time in Casp1/11$^{-/-}$[n=6] and IL-1β/18$^{-/-}$[n=6] mice after i.p. injection with 20 mg kg$^{-1}$ LPS (1,25×LD$_{100}$). Survival (E) and decrease in rectal body temperature (F) were analyzed in function of time in Casp1/11$^{-/-}$[n=17], IL-1β/18$^{-/-}$[n=20] and IL-1β/18/Casp7$^{-/-}$[n=13] mice after i.p. injection with 50 mg kg$^{-1}$ LPS (3,5×LD$_{100}$). Survival (G) and decrease in rectal body temperature (H) were analyzed in function of time in Casp1/11$^{-/-}$[n=6] and IL-1β/18$^{-/-}$[n=6] mice after i.p. injection with 100 mg kg$^{-1}$ LPS (7×LD$_{100}$). Data are means±SEM.

Example 1: IL-1β and IL-18 Deficiency Additively Protect Against a Lethal Dose of LPS To pinpoint the role of the proposed CASP1 substrates in the pathology of endotoxemia, we first analyzed the susceptibility of IL-1β/18- and CASP7-deficient mice. Similar to CASP1/11-deficient mice (Kayagaki et al., 2011), IL-18/18-deficient mice were highly protected against hypothermia and mortality induced by the injection of an $LD_{100}$ (FIG. 1A,B) or $LD_{50}$ (FIG. 6A,B) of LPS, whereas CASP7-deficient mice behaved identical to WT. Because IL-1β/18-deficient mice seemed to suffer slightly less than CASP1/11-deficient mice from the $LD_{100}$ (FIG. 1A,B), we compared the sensitivity of the two strains to supraletal doses. Both genotypes were fully protected against 20 mg kg$^{-1}$ (1.25× $LD_{100}$) of LPS (FIG. 1C and FIG. 6C), but the IL-18/18-deficient mice displayed significantly less hypothermia than CASP1/11-deficient mice (FIG. 6D). However, a higher LPS dose of 3.5× or 7×$LD_{100}$ killed IL-1β/18-deficient mice earlier than CASP1/11-deficient mice (FIG. 1C and FIG. 6E,G), while there was no significant difference in their hypothermic response (FIG. 6F,H). As former studies identified CASP7 as a substrate of CASP1 (Lamkanfi et al., 2009), we generated and tested IL-18/18/CASP7 triple knockout mice. Their susceptibility to LPS ($LD_{100}$) was identical to IL-1β/18-deficient mice (FIG. 1A-C, FIG. 6E), excluding a crucial role for CASP7. Considering the long disputed contribution of both IL-1β and IL-18 in LPS toxicity, we also determined their relative contribution using littermates. Strikingly, LPS-induced mortality was dependent on both IL-1β and IL-18; mice deficient in either IL-1β or IL-18 were partially protected against a lethal dose of LPS, whereas IL-1β/18-deficient mice were completely protected (FIG. 1D). This systematic approach resolves the long dispute on the hierarchical contribution of the several proposed CASP1 substrates (Netea et al., 2000; Joosten et al., 2010; Hochholzer et al., 2000; Lamkanfi et al; 2010, Fantuzzi and Dinarello, 1996) and demonstrates that IL-1β and IL-18 are additively detrimental in endotoxemia, whereas CASP7 is not involved.

Figure 2:
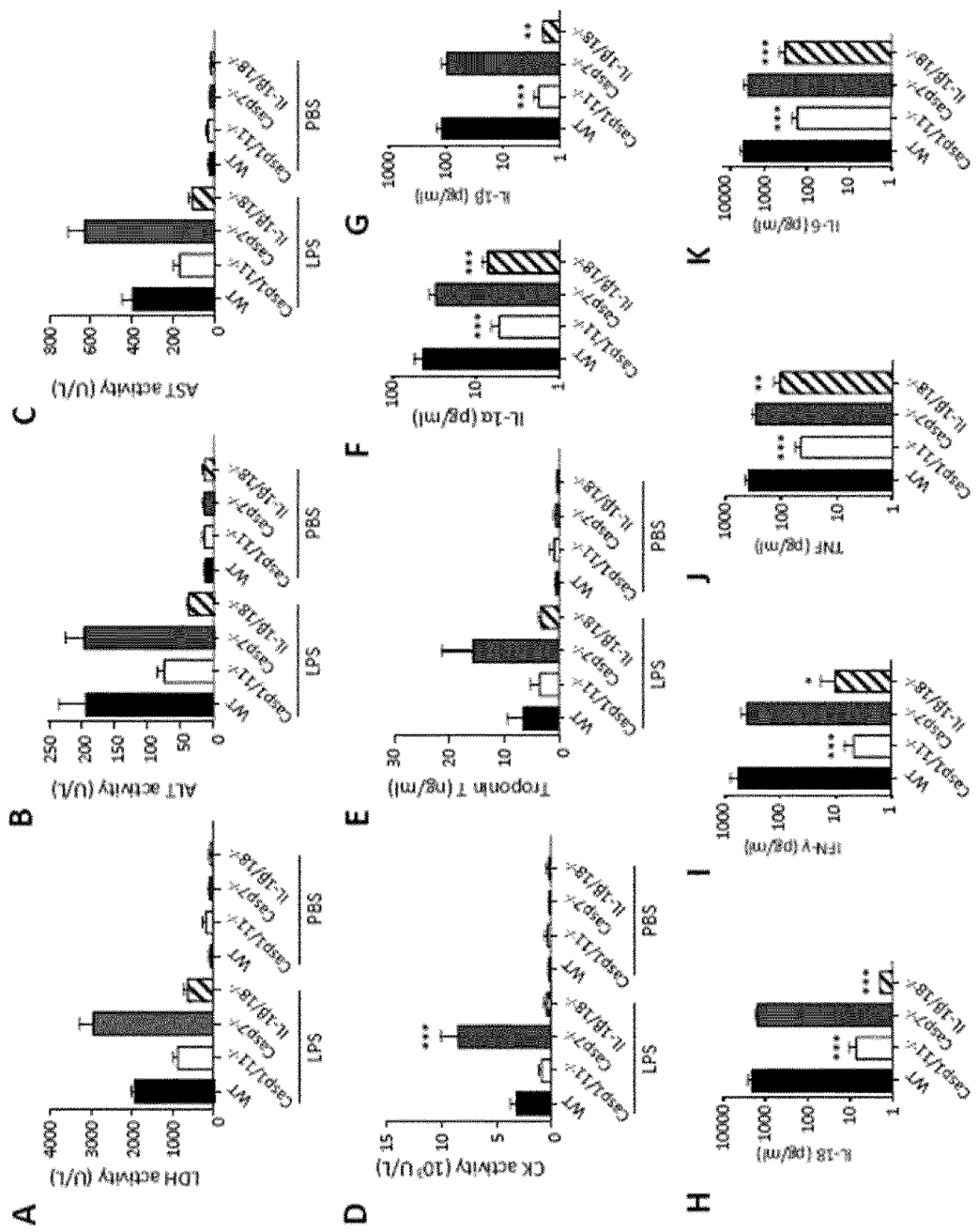
FIG. 2. CASP1 or IL-1β/18 deficiency reduces systemic damage and cytokine levels, in contrast to CASP7-deficiency. Twenty four hours after lethal LPS challenge, 4 mice/group of a total of 10-13 mice/group were sacrificed for phenotyping, the remaining mice were scored for survival up to 96 h to assure consistent phenotypes. Plasma was used for analysis of the levels of LDH (A), liver ALT (B) or AST (C), CK (D), TroponinT (E), IL-1α (F), IL-1β (G), IL-18 (H), IFN-γ (I), TNF (J) and IL-6 (K). Data are means±SEM.
Figure 7:
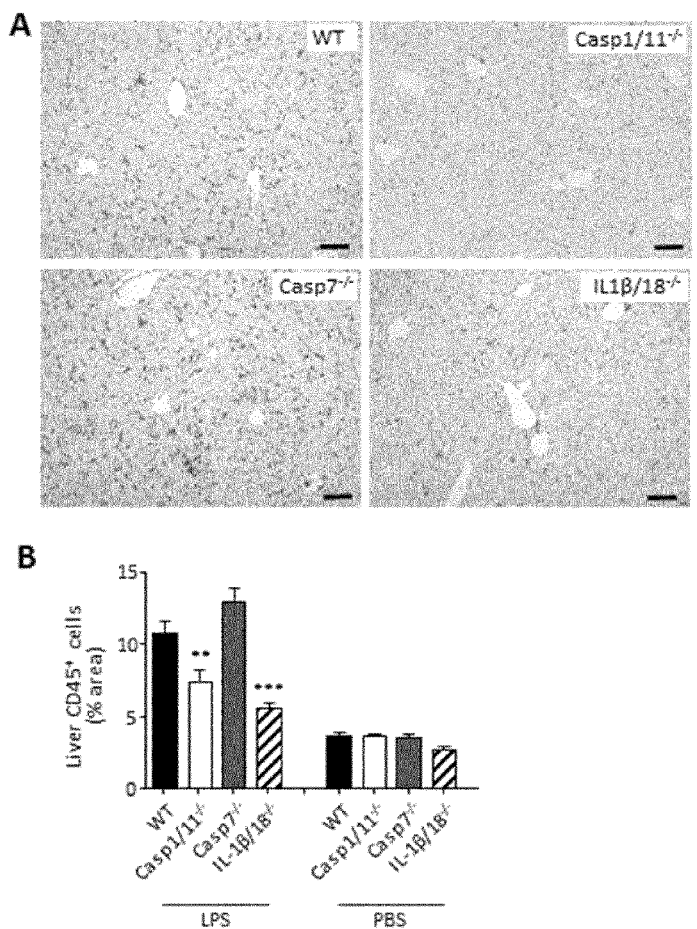
FIG. 7. (A) CD45 staining of liver sections of WT, Casp1/11$^{-/-}$, Casp7$^{-/-}$ and IL-1β/18$^{-/-}$ mice to visualize immune cell infiltration 24 h after lethal LPS challenge (LD$_{100}$, 15 mg kg$^{-1}$). (B) Quantification of relative amounts of CD45$^+$ cells in the liver 24 h after LPS or PBS challenge in WT, Casp1/11$^{-/-}$, Casp7$^{-/-}$ and IL-1β/18$^{-/-}$ mice. Scale bar: 100 μM. Data are means±SE.

Example 2: Protection Against LPS-Induced Lethal Shock is Accompanied by Reduced Systemic Damage and Cytokine Levels To understand the processes leading to death in endotoxemia, we analyzed the knockout strains in more detail, focusing on organ failure, systemic cytokine levels and liver leukocyte infiltration. In accordance with the decreased sensitivity of CASP1/11- and IL-18/18-deficient mice to LPS, their plasma LDH levels, a measure of cellular disintegration, were 50% lower than in WT (FIG. 2A). In contrast, the LDH levels in CASP7-deficient mice were not reduced (FIG. 2A). To identify cellular and organ damage, we determined plasma levels of alanine aminotransferase (ALT), aspartate aminotransferase (AST), creatinine, creatine kinase (CK) and troponin T (TnT). ALT, AST, CK and TnT levels were consistently lower in CASP1/11- and IL-1β/18-deficient mice (FIG. 2B-E), in line with their LPS resistance. Creatinine levels were not elevated, indicating that no severe renal failure had occurred after 24 h yet. In contrast, AST and ALT levels in CASP7 deficient mice were not reduced at all, compared to WT mice (FIG. 2B,C), indicating a similar degree of liver damage. CK and TnT (FIG. 2D,E) were even higher in CASP7-deficient mice, which may indicate increased cardiomyocyte damage. In addition, CASP1/11- and IL-18/18-deficient mice had significantly lower levels of systemic IL-1α, IL-1β, IL-18, IFN-γ, TNF and IL-6 (FIG. 2F-K) 24 h after LPS injection, as well as significantly less CD45-positive white blood cells infiltrated into the liver (FIG. 7A,B). Earlier time points revealed that IL-1β (2 and 6 h), IFNγ (6 h), and to a lesser extent also IL-18, were consistently absent or low in mice that survived an LD$_{50}$ dose of LPS (Table 1). In contrast, CASP7-deficient and WT mice had similar cytokine levels (FIG. 2F-K). In summary, the reduced levels of LDH, ALT, AST, CK and TnT in CASP1/11- and IL-1β/18-deficient mice suggest that the CASP1/IL-1β/IL-18 inflammatory axis contributes to cellular disintegration.

Figure 3:
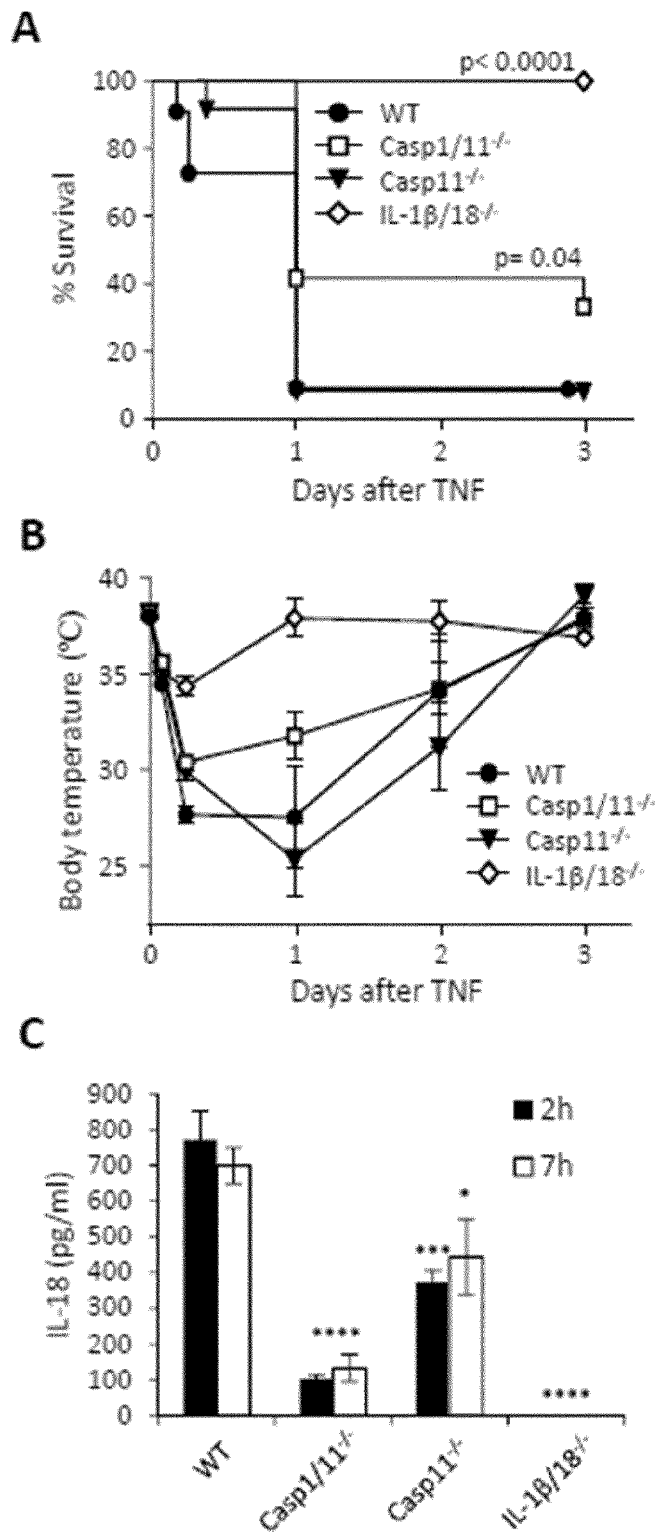
FIG. 3. CASP11- and CASP1/11-deficient mice are not, or only partially, protected against a lethal dose of TNF, while IL-1β/18-deficiency fully protects. Survival (A) and decrease in rectal body temperature (B) were analyzed in function of time in WT [n=20], Casp1/11$^{-/-}$[n=12], Casp11$^{-/-}$[n=12] and IL-1β/18$^{-/-}$[n=10] mice after i.v. injection with 450 μg kg$^{-1}$ TNF (LD$_{100}$). The combined results of two independent experiments are shown. Body temperature data are means±SE. Statistical difference in hypothermia between IL-1β/18$^{-/-}$ vs WT is p<0.001. Levels of IL-18 (C) were determined in plasma 2 and 7 h after TNF injection. Data are means±SEM [n=3 mice/group].

Example 3: IL-1β/18-Deficiency, but not CASP11-Deficiency, Protects Against a Lethal Dose of TNF Next, we analyzed the susceptibility of IL-1β/18-deficient mice for the TNF-induced systemic inflammatory response syndrome (SIRS), in comparison to CASP11- and CASP1/11-deficient mice. Similar to the lethal LPS model, IL-1β/18-deficient mice were completely protected against hypothermia and mortality after a lethal intravenous injection with TNF (FIG. 3A,B). Strikingly, CASP11- and CASP1/11-deficient mice were not, or only partially, protected, respectively (FIG. 3A,B). This may indicate redundancy by other proteases to produce mature IL-1β/18, or, alternatively, that CASP1 (or CASP11) also exerts a protective effect in systemic inflammation. To verify both reasonings we analyzed the levels of IL-1β and -18 in plasma. CASP1-deficiency prevented the maturation of IL-18 (FIG. 3C), while no mature IL-1β could be detected in plasma after TNF injection in any of the genotypes tested, including WT mice. This may suggest that systemic IL-1β levels induced by TNF are below detection limit, rapidly cleared or locally active in a systemically undetectable concentration. CASP11-deficiency only decreased the IL-18 plasma levels by half (FIG. 3C). Hence, this result may indicate a protective role of CASP1 in TNF-induced shock, independent of IL-1β and IL-18 release. In conclusion, deficiency in both IL-1β and IL-18, but not CASP-11 or CASP1/11, fully protects against TNF-induced SIRS.

Figure 4:
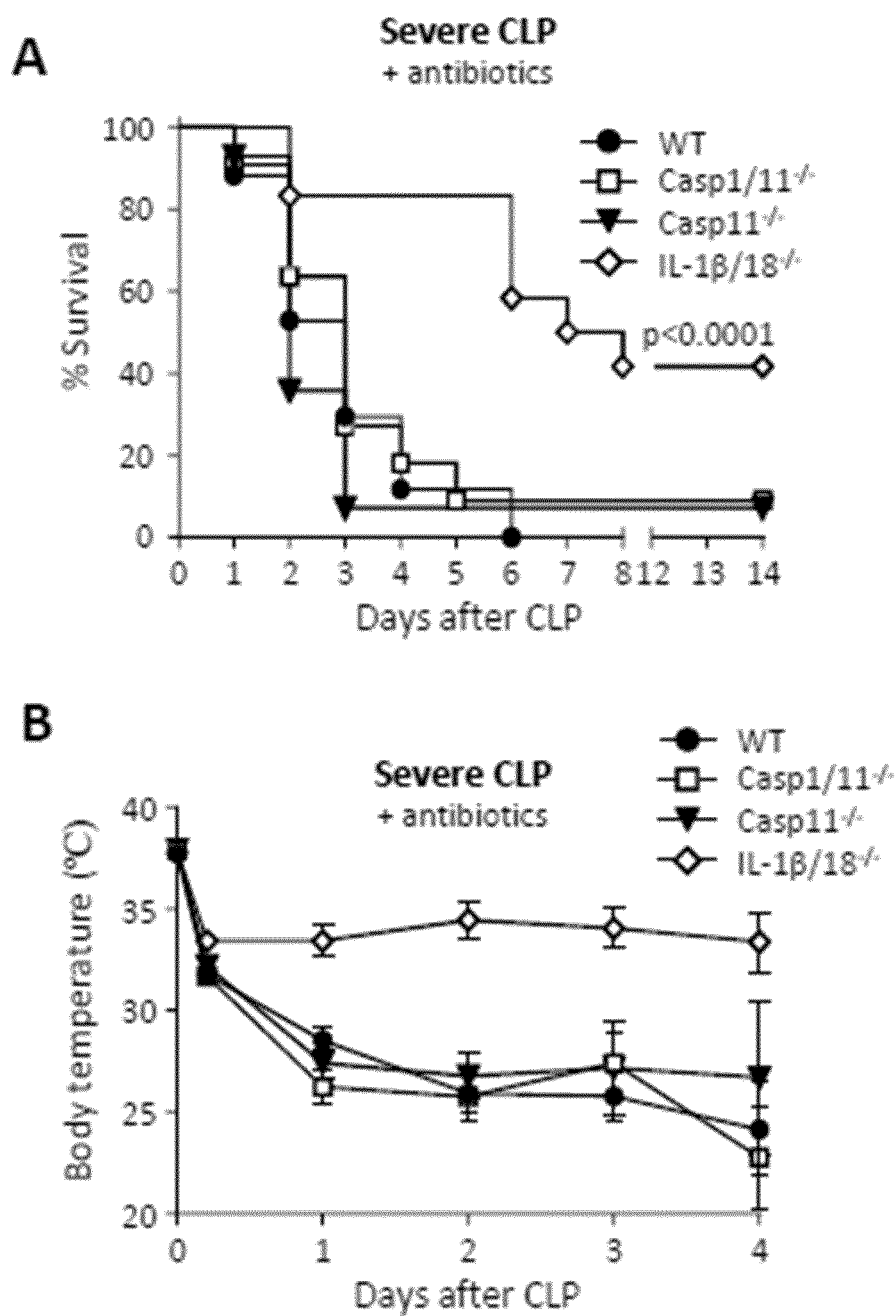
FIG. 4. CASP11- and CASP1/11-deficient mice are not protected against a severe CLP procedure, while IL-1β/18-deficiency protects. Survival (A) and decrease in rectal body temperature (B) were analyzed in function of time in WT [n=17] (C57BL/6 [n=13], IL-1β/18$^{+/+}$ [n=4]), Casp1/11$^{-/-}$ [n=11], Casp11$^{-/-}$[n=14] and IL-1β/18$^{-/-}$[n=12] mice subjected to a severe CLP procedure (LD$_{100}$) and treated with broad-spectrum antibiotics as mentioned in more detail in the materials and methods to the examples. The combined results of four independent experiments are shown. Body temperature data are means±SEM. Statistical difference in hypothermia between IL-1β/18$^{-/-}$ vs WT is p<0.001.
Figure 9:
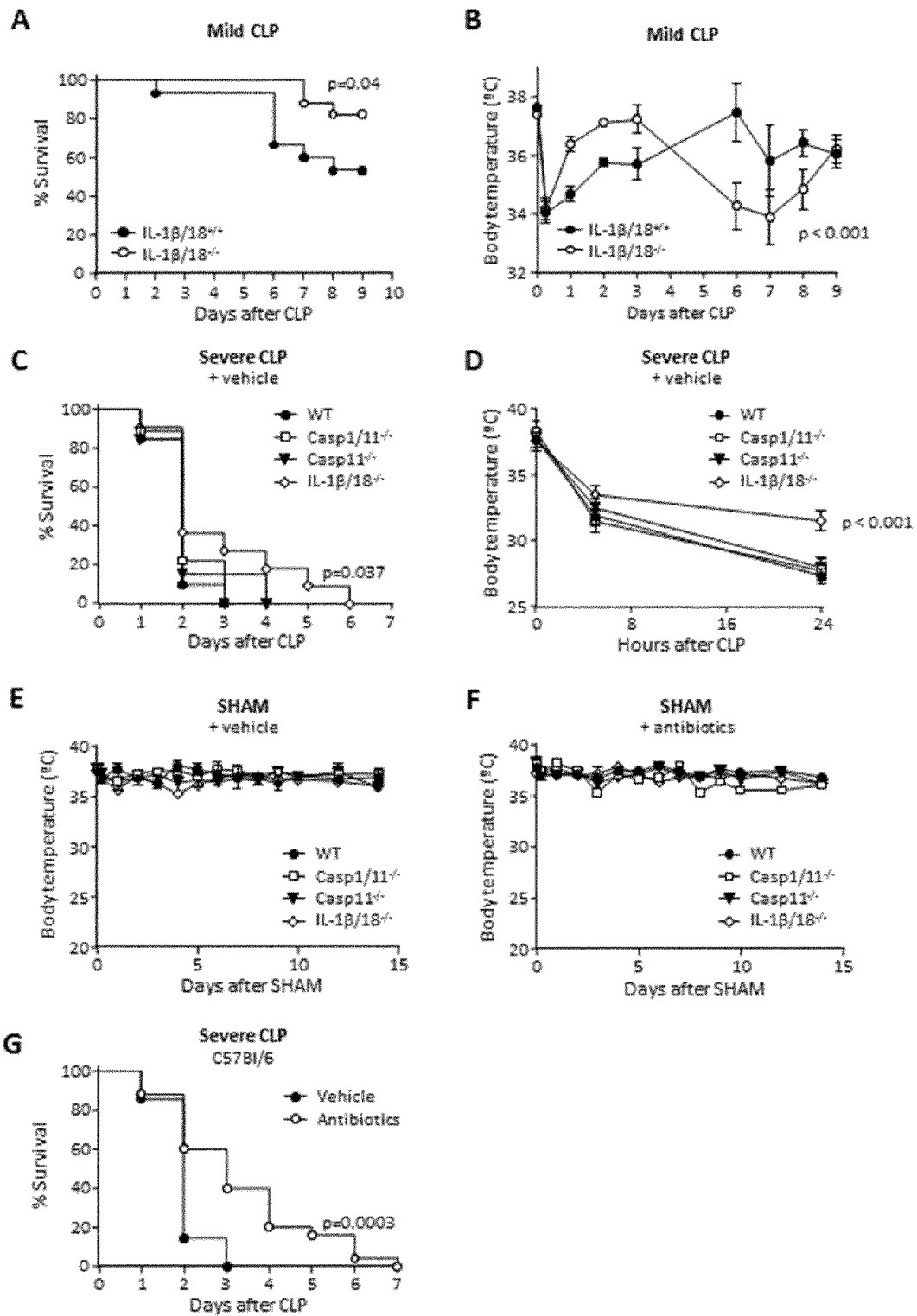
FIG. 9. Survival (A) and decrease in rectal body temperature (B) were analyzed in function of time in IL-1β/18$^{+/+}$ [n=15] and IL1β/18$^{-/-}$[n=17] mice subjected to a mild CLP procedure (LD$_{50}$). The combined results of two independent experiments are shown. Statistical difference in hypothermia between IL-1β/18$^{-/-}$ vs WT is p <0.001. The last two time points reflecting body temperature (day 8 and 9) represent only 5 and 9 mice, respectively. Survival (C) and decrease in rectal body temperature (D) were analyzed in function of time in WT [n=20] (C57BL/6J [n=13], IL-1β/18$^{+/+}$[n=7]), Casp1/11$^{-/-}$[n=9], Casp11$^{-/-}$[n=13] and IL-1β/18$^{-/-[n=}$11] mice subjected to a severe CLP procedure (LD$_{100}$) and treated with vehicle as mentioned in more detail in the materials and methods to the examples. The combined results of four independent experiments are shown. Statistical difference in hypothermia between IL-1β$^{-/-}$ vs WT is p<0.001. Body temperature was analyzed in function of time in WT [n=5] (C57BL/6J [n=3], IL-1β/18$^{+/+}$[n=2]), Casp1/11$^{-/-}$[n=2], Casp11$^{-/-}$[n=4] and IL-1β/18$^{-/-}$[n=3] mice treated with vehicle (E) or antibiotics (F) after a SHAM procedure. Survival (G) was analyzed in function of time in C57BL/6J mice left untreated (Vehicle) [n=28], or treated with antibiotics [n=25] after a severe CLP procedure (LD$_{100}$). The combined results of four independent experiments are shown. Body temperature data are means±SE.
Figure 10:
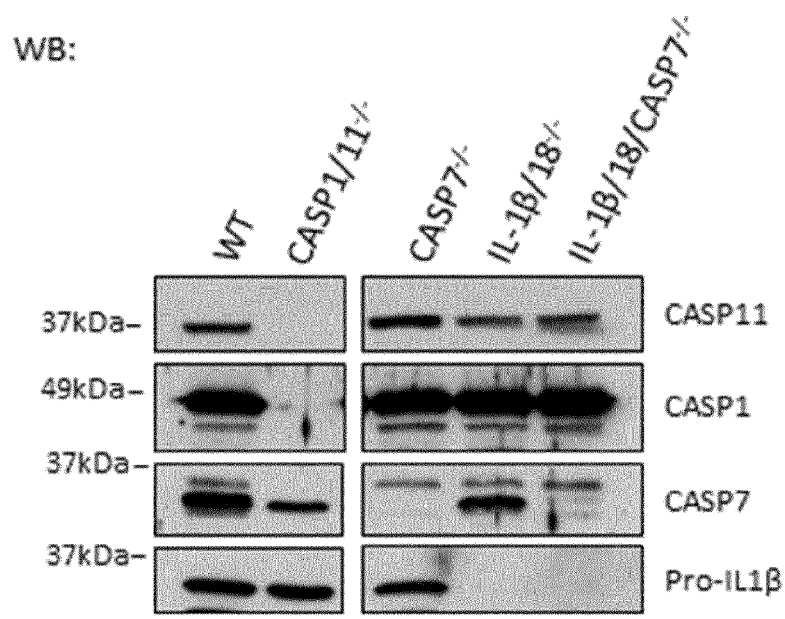
FIG. 10. Spleens were analyzed for CASP11, CASP1, CASP7 and IL-1R expression by Western blotting, 4 hours after i.p. injection with LPS (10 mg kg$^{-1}$) in WT, Casp1/11$^{-/-}$, Casp7$^{-/-}$, IL-1β/18$^{-/-}$, and IL-1β/18/Casp7$^{-/-}$ mice.

Example 4: IL-1β/18-Deficiency, but not CASP11- or -1/11-Deficiency, Protects Against Lethal Cecal Ligation and Puncture Procedures To verify the general significance of our findings, we finally tested two models of cecal ligation and puncture (CLP) with different degrees of severity (referred to as mild and severe CLP). Following the mild CLP procedure (Duprez et al., 2011), IL-1β/18-deficient mice were significantly better protected against hypothermia and mortality than their WT controls (FIG. 9A,B), underscoring their central role in sepsis. In the severe CLP procedure (Godshall et al., 2002), we also treated mice with vehicle or broad-spectrum antibiotics, taking into account the antibiotics treatment in ICUs. In the absence of antibiotics, none of the mice survived the severe CLP procedure (FIG. 9C), in contrast to SHAM operated mice (FIG. 9E). Nevertheless, IL-1β/18-deficient mice survived significantly longer (FIG. 9C) and showed less hypothermia (FIG. 9D) compared with WT animals. Antibiotics treatment significantly prolonged survival in WT mice, compared to vehicle treated mice (FIG. 9G). Strikingly, in combination with antibiotics, the protective effect of IL-1β/18-deficiency was considerably increased compared to vehicle treatment, reflected by significantly less hypothermia and an overall survival of 50% of the mice (FIG. 4A, B). In contrast, the susceptibility of CASP11- or CASP1/11-deficient mice for the severe CLP procedure with or without antibiotics treatment was not different from WT mice (FIG. 4A, B), while all SHAM operated mice survived (FIG. 9F). In summary, only deficiency in both IL-1β and IL-18, but not CASP-11 or -1/11, can protect against both mild and severe CLP-induced morbidity and mortality.

Figure 5:
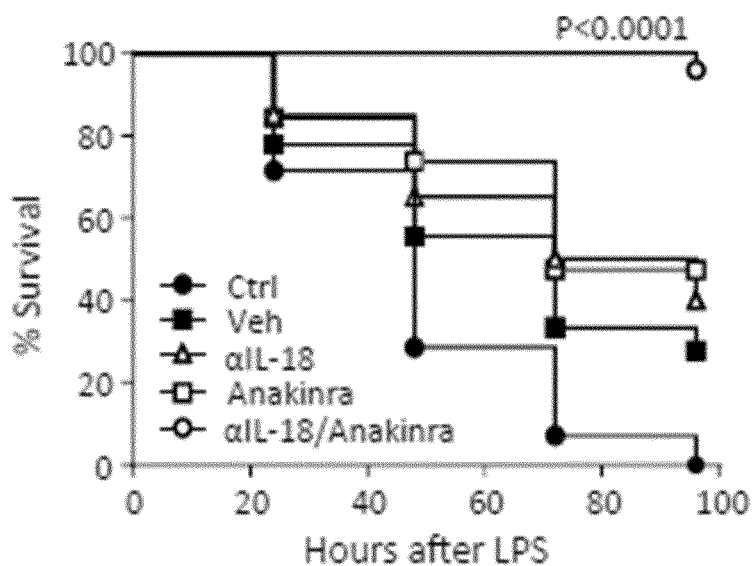
FIG. 5. Therapeutic inhibition of IL-1 and IL-18 signaling completely protects against a lethal LPS challenge. Survival (A) and decrease in rectal body temperature (B) were analyzed in function of time in WT mice left untreated (Ctrl) [n=14], or treated with vehicle (Veh) [n=18], neutralizing IL-18 antibodies (αIL-18) [n=20], Anakinra [n=20] or their combination (αIL-18/Anakinra) [n=24] after i.p. injection with 15 mg kg$^{-1}$ LPS (LD$_{100}$). The combined results of three independent experiments are shown. Body temperature data are means±SEM. Statistical difference in hypothermia between αIL-18, Anakinra and αIL-18/Anakinra vs Veh is p=0.005, p<0.001 and p<0.001, respectively. Statistical difference in survival between vehicle treated (Veh) and untreated (Ctrl) is p=0.042, there is no statistical difference between αIL-18 or Anakinra vs vehicle (Veh).
Figure 5:
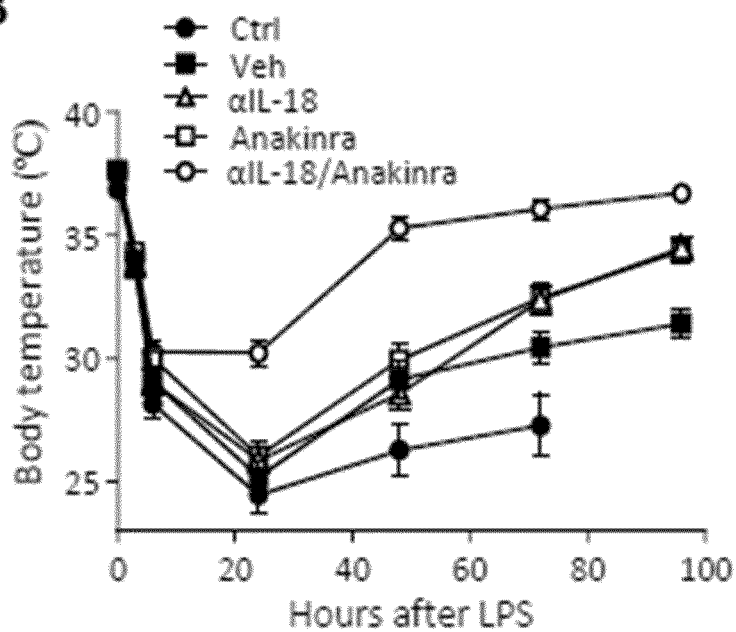
Figure 8:
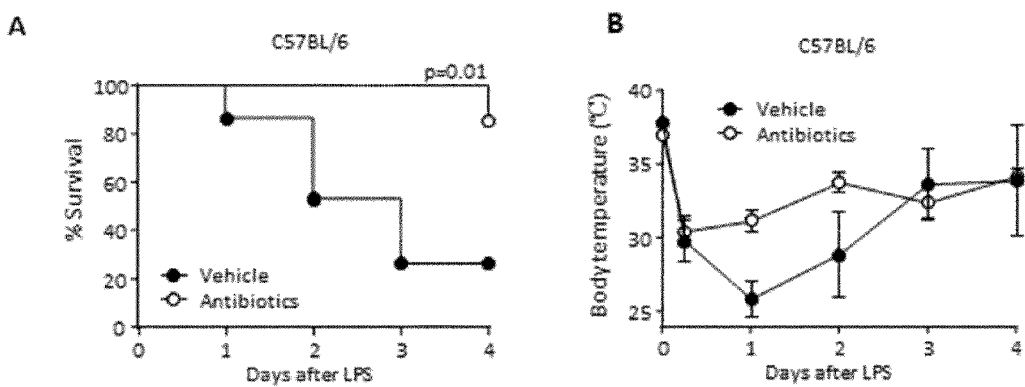
FIG. 8. Survival (A) and decrease in rectal body temperature (B) were analyzed in function of time in C57BL/6J mice left untreated (Vehicle) [n=15] or pretreated with broad spectrum antibiotics for 14 days (prior to the LPS injection) in their drinking water (ciprofloxacin 200 mg L$^{-1}$, ampicillin 1 g L$^{-1}$, metronidazole 1 g L$^{-1}$, vancomycin 500 mg L$^{-1}$) [n=8] after i.p. injection with 15 mg kg$^{-1}$ LPS (LD$_{100}$). Body temperature data are means±SE.

Example 5: Only Combined Therapeutic Inhibition of IL-1 and IL-18 Signaling Protects Against a Lethal Challenge with LPS Of all the transgenic mice we analyzed, only IL-1β/18-deficient mice were consistently protected in all lethal sepsis models. Therefore, we tested the therapeutic potential of simultaneous neutralization of IL-1 and IL-18 signaling. Anakinra (Kineret®) blocks the IL-1R type 1 and is used to treat patients with rheumatoid arthritis (RA) and other auto-immune diseases (Horneff, 2013), while neutralizing IL-18 antibodies are in clinical trials for Crohn's disease (Lochner et al., 2002). As proof of concept we chose the LPS-induced shock model, since this is a well described model mimicking sepsis in humans. Moreover, although LPS-induced shock is generally considered a 'sterile' shock model, we found that antibiotics pretreatment can significantly protect (FIG. 8), indicating the presence of a microbial component, probably due to intestinal ischemia and barrier loss. We treated WT mice twice with αIL-18 or Anakinra, or their combination, 1 h (the time of systemic IL-18 peak, Table 1) and 24 h (the time of systemic IL-18 peak, Table 1) after challenge with LPS. Strikingly, only the combined αIL-18/Anakinra treatment conferred complete protection against hypothermia and mortality after a lethal LPS challenge (FIG. 5A,B). The survival rate of vehicle-treated mice was slightly higher than untreated mice, probably due to rehydration. Single treated mice also showed a slight, but not significant, increased survival compared to vehicle treated mice (FIG. 5A,B). Together, these results corroborate the additive protection we observed in double IL-1β/18-deficient mice compared to single deficient mice (FIG. 1D).

TABLE 1

Overview of cytokine levels analyzed in function of time after a lethal LPS challenge. WT, Casp1/11$^{-/-}$, Casp7$^{-/-}$ and IL-1β/18$^{-/-}$ mice were injected i.p. with PBS or 10 mg kg$^{-1}$ LPS. Serum was collected after 2, 6 and 24 h to measure systemic IL-1α, IL-1β, IL-18, IL-6, IFN-γ and TNF. Results are expressed in pg ml$^{-1}$ and represent means (±SEM).

|  | IL-1α | IL-1β | IL-18 | IL-6 | IFNγ | TNF |
|---|---|---|---|---|---|---|
| PBS 24 h | | | | | | |
| WT | 13.2 ± 6.7 (n = 2) | 0.0 ± 0.1 (n = 4) | 27.8 ± 0 (n = 4) | 8.0 ± 4.2 (n = 2) | 0.0 (n = 1) | 16.9 (n = 1) |

TABLE 1-continued

Overview of cytokine levels analyzed in function of time after a lethal LPS challenge. WT, Casp1/11$^{-/-}$, Casp7$^{-/-}$ and IL-1β/18$^{-/-}$ mice were injected i.p. with PBS or 10 mg kg$^{-1}$ LPS. Serum was collected after 2, 6 and 24 h to measure systemic IL-1α, IL-1β, IL-18, IL-6, IFN-γ and TNF. Results are expressed in pg ml$^{-1}$ and represent means (±SEM).

| | IL-1α | IL-1β | IL-18 | IL-6 | IFNγ | TNF |
|---|---|---|---|---|---|---|
| LPS 2 h | | | | | | |
| WT | 16.9 ± 4.8 (n = 4) | 318.0 ± 51.3 (n = 4) | 200.6 ± 154.1 (n = 4) | >10 000 (n = 4) | 37.9 ± 3 (n = 4) | 942.6 ± 81.6 (n = 4) |
| Casp1/11$^{-/-}$ | 32.1 ± 13.7 (n = 5) | 27.5 ± 10.7 (n = 5) | 2.0 ± 0 (n = 5) | >10 000 (n = 5) | 40.0 ± 2.1 (n = 5) | 885.7 ± 121.1 (n = 5) |
| Casp7$^{-/-}$ | 49.4 ± 34.1 (n = 5) | 283.1 ± 93.3 (n = 5) | 27.2 ± 7.3 (n = 3) | >10 000 (n = 5) | 36.1 ± 2.8 (n = 5) | 492.0 ± 55.9 (n = 5) |
| IL-1β/18$^{-/-}$ | 10.1 ± 4.9 (n = 4) | 2.1 ± 0.2 (n = 4) | 2.0 ± 0 (n = 4) | >10 000 (n = 4) | 32.7 ± 5.2 (n = 4) | 320.8 ± 77.4 (n = 4) |
| LPS 6 h | | | | | | |
| WT | 19.1 ± 9.2 (n = 4) | 270.8 ± 108.1 (n = 4) | 360.9 ± 148 (n = 4) | >10 000 (n = 4) | 1986.2 ± 684.6 (n = 4) | 128.6 ± 23.5 (n = 4) |
| Casp1/11$^{-/-}$ | 63.1 ± 15.8 (n = 6) | 5.7 ± 2 (n = 6) | 2.0 ± 0 (n = 6) | >10 000 (n = 6) | 225.3 ± 61 (n = 6) | 177.0 ± 29.7 (n = 6) |
| Casp7$^{-/-}$ | 218.9 ± 34.7 (n = 5) | 757.1 ± 92.1 (n = 5) | 899.2 ± 213.2 (n = 5) | >10 000 (n = 5) | 5063.2 ± 1126.3 (n = 5) | 189.2 ± 23.1 (n = 5) |
| IL-1β/18$^{-/-}$ | 6.5 ± 3.6 (n = 5) | 2.0 ± 0.3 (n = 5) | 2.0 ± 0 (n = 5) | >10 000 (n = 5) | 134.4 ± 18.7 (n = 5) | 121.7 ± 14.7 (n = 5) |
| LPS 24 h | | | | | | |
| WT | 43.8 ± 11.1 (n = 19) | 91.2 ± 23.7 (n = 18) | 2153.3 ± 426.5 (n = 23) | 3145.7 ± 443.9 (n = 16) | 430.3 ± 179.2 (n = 12) | 377.4 ± 64.5 (n = 12) |
| Casp1/11$^{-/-}$ | 5.4 ± 1.2 (n = 22) | 2.0 ± 0.5 (n = 22) | 7.6 ± 3.4 (n = 27) | 168.6 ± 45.4 (n = 22) | 3.2 ± 2.3 (n = 22) | 45.8 ± 10.9 (n = 22) |
| Casp7$^{-/-}$ | 31.2 ± 5.5 (n = 20) | 95.4 ± 22.3 (n = 19) | 1565.1 ± 180.2 (n = 23) | 2614.1 ± 402.7 (n = 17) | 344.7 ± 104.6 (n = 15) | 294.5 ± 36.4 (n = 16) |
| IL-1β/18$^{-/-}$ | 7.1 ± 1.3 (n = 12) | 2.0 ± 0.3 (n = 10) | 2.0 ± 0 (n = 12) | 326.6 ± 120 (n = 12) | 11.0 ± 11 (n = 4) | 105.1 ± 31 (n = 4) |

REFERENCES

Arend, W. P., Palmer, G., Gabay, C. (2008). IL-1, IL-18, and IL-33 families of cytokines. Immunol Rev 223, 20-38.

Dimitrov, D. S. (2009). Engineered CH2 domains (nano-antibodies). mAbs 1, 26-28.

Duprez, L., Takahashi, N., Van Hauwermeiren, F., Vandendriessche, B., Goossens, V., Vanden Berghe, T., Declercq, W., Libert, C., Cauwels, A., Vandenabeele, P. (2011) Rip kinase-dependent necrosis drives lethal systemic inflammatory response syndrome. Immunity 35, 908-918.

Fantuzzi, G., Dinarello, C. A. (1996). The inflammatory response in interleukin-1 beta-deficient mice: Comparison with other cytokine-related knock-out mice. J Leukoc Biol 59, 489-493.

Fantuzzi, G., Zheng, H., Faggioni, R., Benigni, F., Ghezzi, P., Sipe, J. D., Shaw, A. R., Dinarello, C. A. (1996). Effect of endotoxin in il-1 beta-deficient mice. J Immunol 157, 291-296.

Ferrari, D., Pizzirani, C., Adinolfi, E., Lemoli, R. M., Curti, A., ldzko, M., Panther, E., Di Virgilio, F. (2006). The p2x7 receptor: A key player in il-1 processing and release. J Immunol 176, 3877-3883.

Fischer, E., Marano, M. A., Van Zee, K. J., Rock, C. S., Hawes, A. S., Thompson, W. A., DeForge, L., Kenney, J. S., Remick, D. G., Bloedow, D. C., et al. (1992). Interleukin-1 receptor blockade improves survival and hemodynamic performance in *escherichia coli* septic shock, but fails to alter host responses to sublethal endotoxemia. J Clin Investig 89, 1551-1557.

Franchi, L., Eigenbrod, T., Munoz-Planillo, R., Nunez, G. (2009). The inflammasome: A caspase-1-activation platform that regulates immune responses and disease pathogenesis. Nat Immunol 10, 241-247.

Franchi, L., Munoz-Planillo, R., Reimer, T., Eigenbrod, T., Nigiez, G. (2010). Inflammasomes as microbial sensors. Eur J Immunol 40, 611-615.

Ghayur, T., Banerjee, S., Hugunin, M., Butler, D., Herzog, L., Carter, A., Quintal, L., Sekut, L., Talanian, R., Paskind, M., Wong, W., Kamen, R., Tracey, D., Allen, H. (1997). Caspase-1 processes ifn-gamma-inducing factor and regulates lps-induced ifn-gamma production. Nature 386, 619-623.

Glaccum, M. B., Stocking, K. L., Charrier, K., Smith, J. L., Willis, C. R., Maliszewski, C., Livingston, D. J., Peschon, J. J., Morrissey, P. J. (1997). Phenotypic and functional characterization of mice that lack the type i receptor for il-1. J Immunol 159, 3364-3371.

Godshall, C., Scott, M., Peyton, J., Gardner, S., Cheadle, W. (2002). Genetic background determines susceptibility during murine septic peritonitis. The Journal of surgical research 102, 45-49.

Gu; Y., Kuida, K., Tsutsui, H., Ku, G., Hsiao, K., Fleming, M. A., Hayashi, N., Higashino, K., Okamura, H., Nakanishi, K., Kurimoto, M., Tanimoto, T., Flavell, R. A., Sato, V., Harding, M. W., Livingston, D. J., Su, M. S. (1997). Activation of interferon-gamma inducing factor mediated by interleukin-1 beta converting enzyme. Science 275, 206-209.

Hayashi, S., Lewis, P., Pevny, L., McMahon, A. P. (2002). Efficient gene modulationin mouse epiblast using a sox2cre transgenic mouse strain. Mech. Dev. 119 Suppl 1, S97-S101.

Hochholzer, P., Lipford, G. B., Wagner, H., Pfeffer, K., Heeg, K. (2000). Role of interleukin-18 (il-18) during lethal shock: Decreased lipopolysaccharide sensitivity but normal superantigen reaction in il-18-deficient mice. Infect Immun 68, 3502-3508.

Horneff, G. (2013). Update on biologicals for treatment of juvenile idiopathic arthritis. Expert Opin Biol Ther 13, 361-376.

Hoshino, K., Takeuchi, O., Kawai, T., Sanjo, H., Ogawa, T., Takeda, Y., Takeda, K., Akira, S. (1999). Cutting edge: Toll-like receptor 4 (tlr4)-deficient mice are hyporesponsive to lipopolysaccharide: Evidence for tlr4 as the lps gene product. J Immunol 162, 3749-3752.

Hotchkiss, R. S., Opal, S. (2010). Immunotherapy for sepsis—a new approach against an ancient foe. N Engl J Med 363, 87-89.

Joosten, L. A., Van De Veerdonk, F. L., Vonk, A. G., Boerman, O. C., Keuter, M., Fantuzzi, G., Verschueren, I., Van Der Poll, T., Dinarello, C. A., Kullberg, B. J., Van Der Meer, J. W., Netea, M G. (2010). Differential susceptibility to lethal endotoxaemia in mice deficient in il-1 alpha, il-1beta or il-1 receptor type i. APMIS 118, 1000-1007.

Kanneganti, T. D., Lamkanfi, M., Kim, Y. G., Chen, G., Park, J. H., Franchi, L., Vandenabeele, P., Nunez, G. (2007). Pannexin-1-mediated recognition of bacterial molecules activates the cryopyrin inflammasome independent of toll-like receptor signaling. Immunity 26, 433-443.

Kawai, T., Adachi, O., Ogawa, T., Takeda, K., Akira, S. (1999). Unresponsiveness of myd88-deficient mice to endotoxin. Immunity 11, 115-122.

Kayagaki, N., Warming, S., Lamkanfi, M., Vande Walle, L., Louie, S., Dong, J., Newton, K., Qu, Y., Liu, J., Heldens, S., Zhang, J., Lee, W. P., Roose-Girma, M., Dixit, V. M. (2011). Non-canonical inflammasome activation targets caspase-11. Nature 479, 117-121.

Kolmar, H. (2008) Alternative binding proteins: biological activity and therapeutic potential of cysteine-knot miniproteins. FEBS J. 275, 2684-2690.

Kuida, K., Lippke, J. A., Ku, G., Harding, M. W., Livingston, D. J., Su, M. S., Flavell, R. A. (1995). Altered cytokine export and apoptosis in mice deficient in interleukin-1 beta converting enzyme. Science 267, 2000-2003.

Lamkanfi, M., Moreira, L. O., Makena, P., Spierings, D. C. J., Boyd, K., Murray, P. J., Green, D. R., Kanneganti, T-D. (2009). Caspase-7 deficiency protects from endotoxin-induced lymphocyte apoptosis and improves survival. Blood 113, 2742-2745.

Lamkanfi, M., Sarkar, A., Vande Walle, L., Vitari, A. C., Amer, A. O., Wewers, M. D., Tracey, K. J., Kanneganti, T. D., Dixit, V. M. (2010). Inflammasome-dependent release of the alarmin hmgb1 in endotoxemia. J Immunol 185, 4385-4392.

Li, P., Allen, H., Banerjee, S., Franklin, S., Herzog, L., Johnston, C., McDowell, J., Paskind, M., Rodman, L., Salfeld, J., et al. (1995). Mice deficient in il-1 beta-converting enzyme are defective in production of mature il-1 beta and resistant to endotoxic shock. Cell 80, 401-411.

Lochner, M., Wagner, H., Classen, M., Frster, I. (2002). Generation of neutralizing mouse anti-mouse il-18 antibodies for inhibition of inflammatory responses in vivo. J Immunol Methods 259, 149-157.

Mariathasan, S., Weiss, D. S., Newton, K., McBride, J., O'Rourke, K., Roose-Girma, M., Lee, W. P., Weinrauch, Y., Monack, D. M., Dixit, V. M. (2006). Cryopyrin activates the inflammasome in response to toxins and atp. Nature 440, 228-232.

Miao, E. A., Rajan, J. V., Aderem, A. (2011). Caspase-1-induced pyroptotic cell death. Immunol Rev 243, 206-214.

Netea, M. G., Fantuzzi, G., Kullberg, B. J., Stuyt, R. J., Pulido, E. J., McIntyre, R. C., Jr., Joosten, L. A., Van der Meer, J. W., Dinarello, C. A. (2000). Neutralization of il-18 reduces neutrophil tissue accumulation and protects mice against lethal *escherichia coli* and *salmonella typhimurium* endotoxemia. J Immunol 164, 2644-2649.

Nygren, P-A. (2008) Alternative binding proteins: affibody binding proteins developed from a small three-helix bundle scaffold. FEBS J. 275, 2668-2676.

Ohlsson, K., Bjork, P., Bergenfeldt, M., Hageman, R., Thompson, R. C. (1990). Interleukin-1 receptor antagonist reduces mortality from endotoxin shock. Nature 348, 550-552.

Pelegrin, P., Surprenant, A. (2006). Pannexin-1 mediates large pore formation and interleukin-1 beta release by the atp-gated p2x7 receptor. EMBO J 25, 5071-5082.

Pelegrin, P., Surprenant, A. (2009). The p2x(7) receptor-pannexin connection to dye uptake and il-1beta release. Purinergic Signal 5, 129-137.

Poltorak, A., He, X., Smirnova, I., Liu, M. Y., Van Huffel, C., Du, X., Birdwell, D., Alejos, E., Silva, M., Galanos, C., Freudenberg, M., Ricciardi-Castagnoli, P., Layton, B., Beutler, B. (1998). Defective lps signaling in c3 h/hej and c57bl/10sccr mice: Mutations in tlr4 gene. Science 282, 2085-2088.

Qureshi, S. T., Lariviere, L., Leveque, G., Clermont S., Moore, K. J., Gros, P., Malo, D. (1999). Endotoxin-tolerant mice have mutations in toll-like receptor 4 (tlr4). J Exp Med 189, 615-625.

Rittirsch, D., Huber-Lang, M., Flied, M., Ward, P. (2009). Immunodesign of experimental sepsis by cecal ligation and puncture. Nat Protoc 4, 31-36.

Skerra, A. (2008) Alternative binding proteins: anticalins harnessing the structural plasticity of the lipocalin ligand pocket to engineer novel binding activities. FEBS J. 275, 2677-2683.

Stumpp, M. T. and Amstutz, P. (2007) DARpins: a true alternative to antibodies. Curr. Opin. Drug Discov. Devel. 10, 153-159.

Taveira da Silva, A. M., Kaulbach, H. C., Chuidian, F. S., Lambert, D. R., Suffredini, A. F., Danner, R. L. (1993). Brief report: Shock and multiple-organ dysfunction after self-administration of *salmonella endotoxin*. N Engl J Med 328, 1457-1460.

Tramontano, A., Bianchi, E., Venturini, S., Martin, F., Pessi, A and Sollazzo, M. (1994) The making of the minibody: an engineered beta-protein for the display of conformationally constrained peptides. J. Mol. Recognition 7, 9-24.

Wang, W., Faubel, S., Ljubanovic, D., Mitr, A., Falk, S. A., Kim, J., Tao, Y., Soloviev, A., Reznikov, L. L., Dinarello, C. A., Schrier, R. W., Edelstein, C. L. (2005). Endotoxemic acute renal failure is attenuated in caspase-1-deficient mice. Am. J. Physiol. Renal Physiol. 288, F997-1004.

Wesolowski, J., Alzogaray, V., Reyelt, J., Unger, M., Juarez, K., Urrutia, M., Cauerhiff, A., Danquah, W., Rissiek, B., Scheuplin, F., Schwarz, N., Adriouch, S., Boyer, O., Seman, M., Licea, A., Serreze, D. V., Goldbaum, F. A., Haag, F. and Koch-Nolte, F. (2009). Single domain antibodies: promising experimental and therapeutic tools in infection and immunity. Med. Microbiol. Immunol. 198, 157-174.

The invention claimed is:

1. A method of treating sepsis comprising administering an interleukin-1 receptor antagonist and an interleukin-18 antibody to a subject in need thereof.

2. The method of claim 1, wherein the interleukin-1 receptor antagonist and the interleukin-18 antibody are administered to the subject simultaneously.

3. The method of claim 1, wherein the interleukin-1 receptor antagonist and the interleukin-18 antibody are administered to the subject sequentially.

4. The method of claim 1, wherein said interleukin-1 receptor antagonist is recombinant, non-glycosylated Anakinra.

5. The method of claim 1, wherein said interleukin-1 receptor antagonist is an interleukin-1 receptor antibody.

6. The method of claim 1, wherein said interleukin-1 receptor antagonist neutralizes interleukin-1 receptor.

7. The method of claim 1, wherein said interleukin-18 antibody neutralizes interleukin-18.

8. A method of therapeutically treating sepsis comprising administering an interleukin-1 receptor antagonist and an interleukin-18 antibody to a subject in need thereof.

9. A method of prophylactically treating sepsis comprising administering an interleukin-1 receptor antagonist and an interleukin-18 antibody to a subject in need thereof.

10. The method of claim 8, wherein the interleukin-1 receptor antagonist and the interleukin-18 antibody are administered simultaneously.

11. The method of claim 8, wherein the interleukin-1 receptor antagonist and the interleukin-18 antibody are administered sequentially.

12. The method of claim 11, wherein administration of the interleukin-1 receptor antagonist and administration of the interleukin-18 antibody is separated by a maximum time period of 5 hours.

13. The method of claim 11, wherein administration of the interleukin-1 receptor antagonist and administration of the interleukin-18 antibody is separated by a maximum time period of 4 hours.

14. The method of claim 11, wherein administration of the interleukin-1 receptor antagonist and administration of the interleukin-18 antibody is separated by a maximum time period of 3 hours.

15. The method of claim 11, wherein administration of the interleukin-1 receptor antagonist and administration of the interleukin-18 antibody is separated by a maximum time period of 2 hours.

16. The method of claim 11, wherein administration of the interleukin-1 receptor antagonist and administration of the interleukin-18 antibody is separated by a maximum time period of 1 hour.

17. The method of claim 11, wherein the interleukin-1 receptor antagonist and the interleukin-18 antibody are administered directly one after the other.

* * * * *